United States Patent [19]

Evans et al.

[11] 4,374,742

[45] Feb. 22, 1983

[54] NOVEL LUBRICANT ADDITIVES

[75] Inventors: Samuel Evans; Michael Rasberger; Eberhard Gegner, all of Riehen, Switzerland

[73] Assignee: Ciba-Geigy Corporation, Ardsley, N.Y.

[21] Appl. No.: 268,309

[22] Filed: May 29, 1981

Related U.S. Application Data

[63] Continuation of Ser. No. 64,238, Aug. 6, 1979, abandoned.

[30] Foreign Application Priority Data

Aug. 18, 1978 [CH] Switzerland ................... 8790/78

[51] Int. Cl.³ ........................ C07F 7/08; C07F 7/10
[52] U.S. Cl. ........................ 252/48.4; 556/413; 556/414; 556/419; 556/423; 556/427; 556/438; 556/440; 556/445; 556/446; 556/449; 260/398; 260/399; 260/404; 252/49.6; 252/51.5 R
[58] Field of Search ............... 556/413, 414, 419, 423, 556/427, 438, 440, 445, 446, 449; 260/398, 399, 404; 252/48.4, 49.6, 51.5 R

[56] References Cited

U.S. PATENT DOCUMENTS 4,282,366 8/1981 Eudy ................................ 556/413

FOREIGN PATENT DOCUMENTS 2030581 4/1980 United Kingdom ............... 556/413

*Primary Examiner*—Paul F. Shaver
*Attorney, Agent, or Firm*—Harry Falber

[57] ABSTRACT

Novel organic phenol-containing silicon compounds of the formula

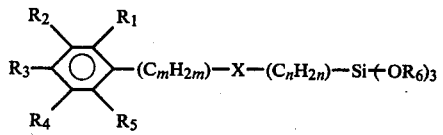

are disclosed.

These compounds are suitable for use as lubricant additives.

11 Claims, No Drawings

NOVEL LUBRICANT ADDITIVES

This is a continuation of application Ser. No. 064,238 filed on Aug. 6, 1979, now abandoned.

The present invention relates to novel phenol-containing silanes, process for their manufacture, their use as additives in lubricants, and the lubricants stabilised therewith.

Different additives are normally added to mineral and synthetic lubricants in order to improve their performance properties. In particular there is a need for additives which protect lubricant from attack by atmospheric oxygen and thereby prolong their life. The inhibition of oxidation is also advantageous as regards corrosion, as the formation of acid oxidation products is substantially prevented.

The present invention is based on the observation that a very good antioxidising and anticorrosive effect can be obtained in lubricants by the addition of phenol-containing silanes.

The compounds of the invention have the formula I

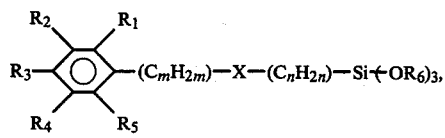

wherein one of $R_1$ and $R_3$ is hydrogen and the other is OH, each of $R_2$, $R_4$ and $R_5$ independently is $C_1$–$C_{12}$alkyl, $C_5$–$C_7$cycloalkyl, $C_6$–$C_{10}$aryl or $C_7$–$C_9$aralkyl, and $R_4$ and $R_5$ are also hydrogen, $R_6$ is $C_1$–$C_{18}$alkyl, each of m and n independently is an integer from 0 to 6, X is the direct bond, —O—, —S—, —N($R_7$)—, —Q—$R_8$— or

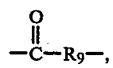

wherein $R_7$ represents hydrogen, $C_1$–$C_{12}$alkyl, phenyl or a group of the formula II

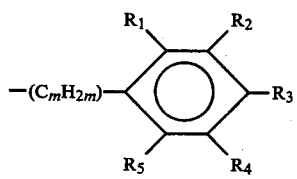

wherein $R_1$, $R_2$, $R_3$, $R_4$, $R_5$ and m are as defined above, Q is —O— or —NH—, $R_8$ represents a group of the formula III

—CH$_2$—CH(OR$_{10}$)—CH$_2$—O—     (III)

wherein $R_{10}$ is hydrogen, $C_1$–$C_{12}$alkyl or a group of the formula IV

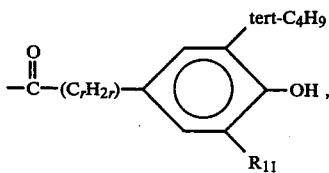

wherein r is an integer from 0 to 6, $R_{11}$ is hydrogen, $C_1$–$C_{12}$alkyl, $C_5$–$C_7$cycloalkyl, $C_6$–$C_{10}$aryl or $C_7$–$C_9$aralkyl, and $R_9$ is —O—, —NH—, —OH.H$_2$N—, —O—CH$_2$CH$_2$—S—,

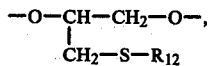

—O—$R_8$—, or a group of the formula V

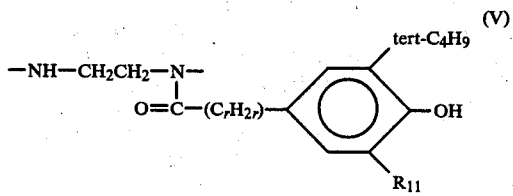

wherein $R_8$, $R_{11}$ and r are as defined above, and $R_{12}$ is $C_1$–$C_{18}$alkyl, $C_5$–$C_7$cycloalkyl, $C_6$–$C_{10}$aryl, $C_7$–$C_9$aralkyl or a group of the formulae VI or VII —(C$_u$H$_{2u}$)—COOR$_{10}$     (VI)

or

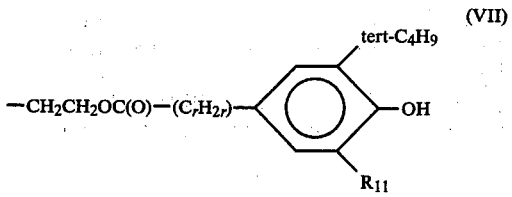

wherein u is an integer from 1 to 6 and $R_{10}$, $R_{11}$ and r are as defined above.

One of $R_1$ and $R_3$, preferably $R_3$, is OH and the other is hydrogen.

$R_2$, $R_4$, $R_5$ and $R_{11}$ as $C_1$–$C_{12}$alkyl are e.g. methyl, ethyl, isopropyl, sec-butyl, tert-butyl, tert-pentyl, n-hexyl, 1,1,3,3-tetramethylbutyl, n-nonyl or 1,1,3,3,5,5-hexamethylhexyl. $R_2$ contains preferably 1 to 8 carbon atoms and is in particular methyl or tert-butyl. $R_4$ and $R_{11}$ are preferably $C_1$–$C_4$alkyl and, in particular, tert-butyl. $R_5$ as alkyl contains in particular 1 to 6 carbon atoms, but is preferably hydrogen.

Cycloalkyl represented by $R_2$, $R_4$, $R_5$, $R_{11}$ and $R_{12}$ is e.g. cyclopentyl, xcyclohexyl or cycloheptyl.

$R_2$, $R_4$, $R_5$, $R_{11}$ and $R_{12}$ as $C_6$–$C_{10}$aryl are e.g. phenyl, α- or β-naphthyl.

$R_2$, $R_4$, $R_5$, $R_{11}$ and $R_{12}$ as $C_7$–$C_9$aryl can be e.g. benzyl, α-phenylethyl or α,α-dimethylbenzyl.

$R_6$ and $R_{12}$ as $C_1$–$C_{18}$alkyl are e.g. methyl, ethyl, n-propyl, isopropyl, n-butyl, n-hexyl, n-octyl, 2-ethylhexyl, n-nonyl, n-dodecyl or n-octadecyl. In particular, $R_6$ is methyl or ethyl.

m has a value from 0 to 6, preferably from 0 to 4 and in particular from 1 to 3. n can be an integer from 0 to 6, but is preferably 3.

$R_7$ and $R_{10}$ as $C_1$–$C_{12}$alkyl are e.g. methyl, ethyl, isopropyl, n-propyl, n-butyl, sec-butyl, tert-butyl, n-pentyl, n-hexyl, n-octyl, 2-ethylhexyl, n-nonyl or n-dodecyl. $R_{10}$ preferbly contains 1 to 4 carbon atoms.

In addition to hydrogen, $R_7$ preferably also represents the group of the formula II, wherein m, $R_1$, $R_2$, $R_3$, $R_4$ and $R_5$ have the given meanings.

Q is —O— and, in particular, —NH—, and r can be integer from 0 to 6, especially from 0 to 4, and is preferably 2.

The preferred meanings of $R_9$ are in particular —NH—, —O—$CH_2CH_2$—S— and —$OR_8$—. However, compounds in which $R_9$ is —$OH.H_2N$— are also of interest.

If X is the direct bond, the value of m is preferably 0 and that of n is preferably 2 or 3.

Interesting compounds are those of the formula I wherein $R_1$ is hydrogen, $R_3$ is OH and each of $R_2$, $R_4$ and $R_6$ independently is $C_1$-$C_{12}$alkyl and $R_4$ is also hydrogen, $R_5$ is hydrogen or $C_1$-$C_6$alkyl, m is an integer from 0 to 4 and n is 3, X is the direct bond, —O—, —S—, —N($R_7$)—, —Q—$R_8$— or

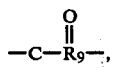

wherein $R_7$ is hydrogen or a group of the formula II, in which $R_1$, $R_2$, $R_3$, $R_4$, $R_5$ and m are as defined above, Q is —O— or —NH—, $R_8$ is a group of the formula III, wherein $R_{10}$ is hydrogen, $C_1$-$C_{12}$alkyl or a group of the formula IV, wherein r is an integer from 0 to 4, $R_{11}$ is $C_1$-$C_{12}$alkyl, and $R_9$ is —O—, —NH—, —$OH.H_2N$—, —O—$CH_2CH_2$—S—, —$OR_8$— or a group of the formula V, wherein $R_8$, r and $R_{11}$ have the above meanings.

Preferred compounds are those of the formula I wherein $R_1$ $R_6$ is methyl or ethyl, m is an integer from 0 to 4 and n is 3, X is the direct bond, —O—, —S—, —N($R_7$)— or

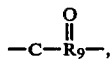

wherein $R_7$ is a group of the formula II, in which $R_1$, $R_2$, $R_3$, $R_5$ and m are as defined above, $R_9$ is —NH—, —O—$CH_2$—$CH_2$—S— or —$OR_8$—, wherein $R_8$ is a group of the formula III, in which $R_{10}$ is hydrogen or a group of the formula IV, wherein r is 2 and $R_{11}$ is $C_1$-$C_4$alkyl.

Particularly preferred compounds are those of the formula I, wherein $R_1$ and $R_5$ are hydrogen, $R_3$ is OH, $R_2$ is methyl or tert-butyl, $R_4$ is tert-butyl, $R_6$ is methyl or ethyl, m is an integer from 1 to 3 and n is 3, X is the direct bond, —O—, —S—, —N($R_7$)— or

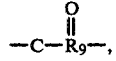

wherein $R_7$ is a group of the formula II, in which $R_1$, $R_2$, $R_3$, $R_4$, $R_5$ and m have the above meanings, $R_9$ is —NH— or —$OR_8$—, wherein $R_8$ is a group of the formula III, in which $R_{10}$ is hydrogen.

Interesting compounds are also those of the formula I, wherein X is —NH—$R_8$— or

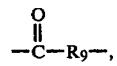

in which $R_8$ is as defined above and $R_9$ is —$OH.H_2N$—.

Examples of compounds of the formula I are:

| (A) | ![structure: HO—(tert-C4H9)2-C6H2—(CH2)m—Y—(CH2)3—Si(OR6)3] | | |
|---|---|---|---|
| (1) | Y: —S— | $R_6$: —$CH_3$ | m:1 |
| (2) | Y: —O—$CH_2$—CH(OH)—$CH_2$—O— | $R_6$: —$CH_3$ | m:1 |
| (3) | Y: —N(CH2-C6H2(tert-C4H9)2-OH)— | $R_6$: —$C_2H_5$ | m:1 |
| (4) | Y: —C(O)—NH— | $R_6$: —$C_2H_5$ | m:2 |
| (5) | Y: $COOH.H_2N$— | $R_6$: —$C_2H_5$ | m:2 |
| (6) | Y: — | $R_6$: —$CH_3$ | m:2 |
| (7) | Y: —COO—$CH_2$—CH(OH)—$CH_2$—O— | $R_6$: —$CH_3$ | m:2 |
| (8) | Y: —COO—$CH_2$—CH(O—C(O)—$CH_2CH_2$—C6H2(tert-C4H9)2—CH)—$CH_2$—O— | $R_6$: —$CH_3$ | m:2 |
| (9) | Y: —COO—$CH_2$—$CH_2$—S— | $R_6$: —$CH_3$ | m:2 |
| (10) | Y: —COO—CH(CH2—S—CH2—COO—$C_8H_{17}$)—$CH_2$—O— | $R_6$: —$CH_3$ | m:2 |

| | | |
|---|---|---|
| -continued | | |
| (11) Y: —C(O)—NH—(CH$_2$)$_2$—N— 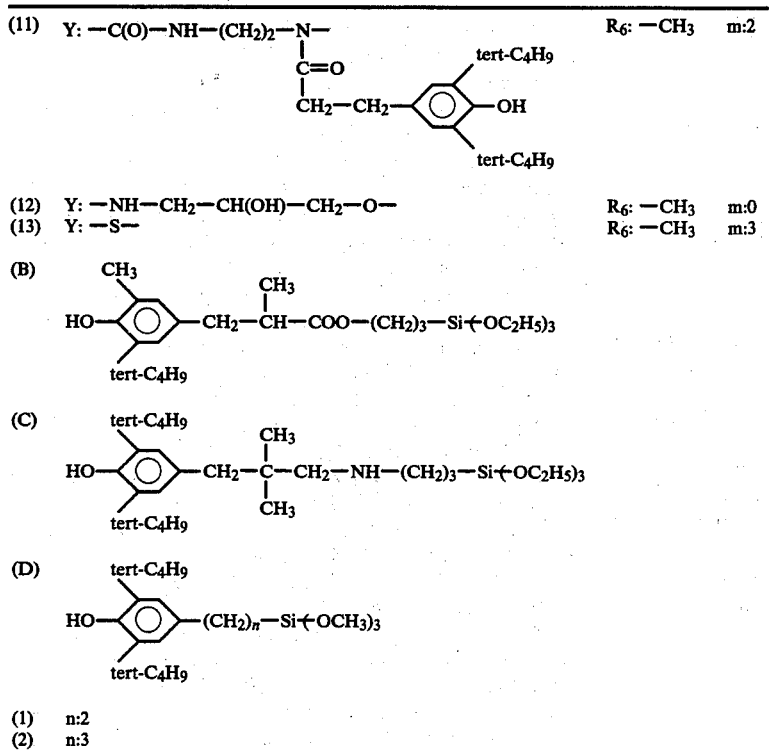 | R$_6$: —CH$_3$ | m:2 |
| (12) Y: —NH—CH$_2$—CH(OH)—CH$_2$—O— | R$_6$: —CH$_3$ | m:0 |
| (13) Y: —S— | R$_6$: —CH$_3$ | m:3 |
| (B) 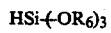 | | |
| (C) 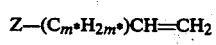 | | |
| (D) 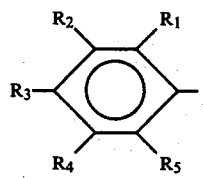 | | |
| (1) n:2 | | |
| (2) n:3 | | |

The compounds of the formula I are obtained by known methods, for example by Michael addition or esterification or transesterification reactions. All reactions described hereinafter are preferably carried out under nitrogen.

The compounds of the formula I, wherein X is the direct bond, can be obtained e.g. by the reaction of a silane of the formula VIII $$HSi(-OR_6)_3 \qquad (VIII)$$

with a compound of the formula IX $$Z-(C_{m^*}H_{2m^*})CH=CH_2 \qquad (XI)$$

wherein Z is a group of the formula X

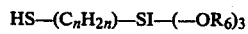

in the presence of a catalyst, such as hexachloroplatinic acid, preferably in a solvent, for example an alcohol, such as isopropanol.

In the formulae VIII, IX and X, the substituents R$_1$, R$_2$, R$_3$, R$_4$, R$_5$ and R$_6$ have the meanings given above and m* is an integer from 0 to 4.

A compound of the formula I, in which X is —O— or —S—, is for example the reaction product of a mercaptan of the formula XI $$HS-(C_nH_{2n})-SI-(-OR_6)_3 \qquad (XI)$$

and a compound of the formula IX, preferably in the presence of a radical initiator, such as azoisobutyronitrile and a solvent, such as tetrahydrofurane. Compounds of the formula I, wherein m is 1, are most simply obtained by benzylation of a compound of the formula XI with a benzylating agent of the formula XII $$Z-R_{13} \qquad (XII)$$

wherein Z is a group of the formula (X) as defined above, and R$_{13}$ is hydrogen or —CH$_2$Cl, —CH$_2$NR$_{14}$R$_{15}$ or —CH—S—C(S)—NR$_{14}$R$_{15}$, wherein R$_{14}$ and R$_{15}$ are alkyl or together with the nitrogen atom to which they are attached form a 5- or 6-membered ring. When R$_{13}$ is hydrogen, the known benzylation is carried out in the presence of formaldehyde and an acid. In the formulae X, XI and XII, the symbols n, Z, R$_1$, R$_2$, R$_3$, R$_4$, R$_5$ and R$_6$ have the given meanings. Reactions of this type are described e.g. in U.S. Pat. No. 3,281,334.

Compounds of the formula I, wherein X is —N(R$_7$)—, can be obtained in known manner by reacting an amine of the formula XIII $$HN(R_7)-C_nH_{2n})Si-(-OR_6)_3 \qquad (XIII)$$

with an aldehyde of the formula XIV $$Z-(C_{m^{}}H_{2m^{}})CHO \qquad (XIV)$$

in the presence of a reduction system, such as H$_2$/Pd. If R$_7$ in formula (XIII) is a group of the formula II, these compounds can be obtained e.g. from amines of the formula (XIII), wherein R$_7$ is hydrogen, with a phenol of the formula (XII), wherein R$_{13}$ is hydrogen, in the presence of formaldehyde. In the formulae XIII, XIV and II, the symbols Z, $R_6$, $R_7$, m and n have the meanings given above. m** is 0 to 5.

If X is $-O-R_8-$ in compounds of the formula I, these latter are obtained e.g. by the reaction of an epoxide of the formula XV

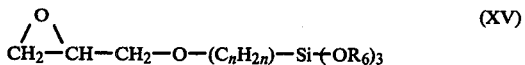 (XV)

with an alcohol or amine of the formula XVI $$Z-(C_mH_{2m})QH \qquad (XVI)$$

preferably in a solvent, such as benzene, toluene or xylene. In these formulae, m, n, Z, $R_6$ and Q are as defined previously.

The resulting compounds (in which X is $-Q-R_8$ and $R_8$ is a group of the formula III, in which $R_{10}$ is hydrogen) can be alkylated or esterified in known manner to produce analogous products in which $R_{10}$ is alkyl or a group of the formua IV, wherein all the symbols have the meanings given above.

Substitution of compounds of the formula XVII $$Z-(C_mH_{2m})-COOH \qquad (XVII)$$

or those of the formula XVIII $$NaS-CH_2COOR_{12} \qquad (XVIII)$$

for the compounds of the formula XVI in the above reaction, in which case the reaction products obtained from compounds of the formulae XVI and XVIII are subsequently esterified in known manner with compounds of the formula XVII or the lower alkyl esters thereof, yields compounds of the formula I, wherein X is $-C(O)-R_9$ and $R_9$ is $-O-R_8-$ or $-O-CH(CH_2-S-R_{12})-CH_2-O$. Reaction of the hydroxy compound of the $-O-R_8-$ type with a compound of the formula XVII or the lower alkyl ester thereof yields compounds of the formula I, wherein X is $-C(O)-R_9-$, $R_9$ is $-O-R_8-$ and $R_8$ is a group of the formula III, wherein $R_{10}$ is a group of the formula IV. Unless otherwise indicated, all the symbols referred to are as defined previously.

Compounds of the formula I, wherein X is $-C(O)-R_9$, and $R_9$ is $-O-$ or $-O-CH_2CH_2-S-$ are most simply obtained by reacting a chloride of the formula XIX $$(R_6O)_3-Si-(-C_nH_{2n})-Cl \qquad (XIX)$$

with a compound of the formula XX $$Z-(C_mH_{2m})COOR_{16} \qquad (XX)$$

wherein $R_{16}$ is Na or $-CH_2CH_2-SH$, and the other symbols of the formulae XIX and XX have the given meanings.

The compounds of the formula I, wherein X is $-C(O)-R_9-$, and $R_9$ is $-NH-$ or a group of the formula V, are obtained e.g. by reaction of an amine of the formula XXI $$R_{17}-NH-(C_nH_{2n})-Si-(-OR_6) \qquad (XXI)$$

wherein $R_{17}$ is hydrogen or $H_2N-(CH_2)_2-$, with a lower alkyl ester of the acids of the formula XVII, in the presence of a basic catalyst, such as lithium amide, in an aprotic solvent such as benzene, toluene or xylene.

Compounds of the formula I, wherein X is $-C(O)-R_9-$ and $R_9$ is $-OH.H_2N-$, are obtained by reacting an amine of the formula XXI with a carboxylic acid of the formula XVII, without a catalyst in an aprotic solvent for example toluene or dioxane.

The starting materials of the formulae VIII to XXI employed for the known methods of manufacture described above are known or, if they are new, can be obtained in analogous manner. Many of these compounds are commercially available.

Even when used in very insignificant amounts, the compounds of the formula I act as stabilisers against oxidation and corrosion in lubricants. Accordingly, mineral and synthetic lubricating oils, as well as mixtures thereof, which contain 0.001 to 5 percent by weight, based on the lubricant, and preferably 0.02 to 3 percent by weight, of a compound of the formula I, exhibit excellent lubricating properties which become evident due to the greatly reduced signs of wear of the friction surface to be lubricated. The suitable lubricants are known to the skilled person and are described for example in the "Schmiermittel Taschenbuch" (Hüthig Verlag, Heidelberg, 1974).

The lubricating oil formulation can contain still further additives which are added to improve certain performance properties, such as antioxidants, metal deactivators, rust inhibitors, viscosity index improvers, pour-point depressors, dispersant/surfactants and other wear resisting additives.

Examles of antioxidants are:
(a) Alkylated and non-alkylated aromatic amines and mixtures thereof, for example: dioctyldiphenylamine, 2,2,3,3-tetramethylbutylphenyl-α- and -β-naphthylamines, phenotriazine, dioctylphenothiazine, phenyl-α-naphthylamine, N,N'-di-sec-butyl-p-phenylenediamine.
(b) Sterically hindered phenols, for example: 2,6-di-tert-butyl-p-cresol, 4,4'-bis-(2,6-diisopropylphenol), 2,4,6-triisopropylphenol, 2,2'-thio-bis-(4-methyl-6-tert-butylphenol), 4,4'-methylene-bis-(2,6-di-tert-butylphenol).
(c) Alkyl-, aryl- or aralkylarylphosphites, for example: trinonylphosphite, triphenylphosphite, diphenyldecylphosphite.
(d) Esters of thiodipropionic acid or thiodiacetic acid, for example: dilaurylthiodipropionate or dioctylthiodiacetate.
(e) Salts of carbamic and dithiophosphoric acids, for example: antimony diamyldithiocarbamate, zinc diamyldithiophosphate.
(f) A combination of two or more of the above antioxidants, for example: an alkylated amine and a sterically hindered phenol.

Examples of metal deactivators are:
(a) for copper, e.g.: benzotriazole, tetrahydrobenzotriazole, 2-mercaptobenzotriazole, 2,5-dimercaptothiadiazole, salicylidene propylenediamine, salts of salicylaminoguanidine.
(b) for lead, e.g.: sebacid acid derivatives, quinizarine, propyl gallate.
(c) A combination of two or more of the above additives.

Examples of rust inhibitors are:
(a) Organic acids, the esters, metal salts and anhydrides thereof, e.g.: N-oleyl-sarcosine, sorbitan mono-oleate, lead naphthenate, dodecenylsuccinic anhydride.

(b) Nitrogen-containing compounds, for example:
  I. Primary, secondary or tertiary aliphatic or cycloaliphatic amines and amine salts of organic and inorganic acids, for example, oil-soluble alkylammonium carboxylates.
  II. Heterocyclic compounds, e.g. substituted imidazolines and oxazolines.
(c) Phosphorus-containing compounds, for example: amine salts of phosphoric acid partial esters.
(d) Sulfur-containing compounds, for example: barium dinonylnaphthalenesulfonates, calcium petroleum sulfonates.
(e) Combinations of two or more of the above additives.

Examples of Viscosity index improvers are:
polymethylacrylates, vinyl pyrrolidone/methacrylate copolymers, polybutene, olefin copolymers, styrene/acrylate copolymers.

Examples of pour-point depressors are:
polymethacrylates, alkylated naphthalene derivatives.

Examples of dispersants/surfactants are:
polybutenylsuccinic imides, polybutenylphosphonic acid derivatives, superbasic magnesium, calcium and barium sulfonates and phenolates.

Examples of wear resisting additives are:
compounds which contain sulfur and/or phosphorus and/or halogen, such as sulfurised vegetable oils, zinc dialkyldithiophosphates, tritolylphosphate, chlorinated paraffins, alkyl- and aryldisulfides.

The following Examples describe in closer detail the manufacture of the compounds to be employed as stabilisers in the lubricants according to the invention, and also the use and action of the lubricant compositions.

EXAMPLE 1

A solution of γ-aminopropyltriethoxysilane (22.1 g, 0.1 mole) in 50 ml if isopropanol is added dropwise in the course of 30 minutes to 40.6 g (0.2 mole) of 2,6-di-

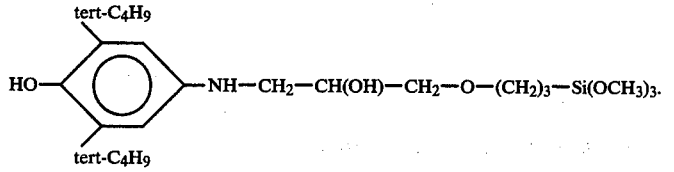

tert-butylphenol and 6 g (0.2 mole) of para-formaldehyde in 100 ml of isopropanol. The reaction mixture is kept for 16 hours at reflux temperature, then cooled and dried over sodium sulfate. The filtrate solvent is evaporated. The residue consists of 58.5 g of a clear orange oil having the following structure:

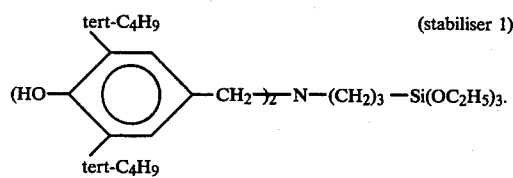

(stabiliser 1)

EXAMPLE 2

1 g of lithium amide is added at 80° C. under nitrogen to 29.2 g (0.1 mole) of methyl 4-hydroxy-3,5-di-tert-butylphenylpropionate and 22.1 g (0.1 mole) of γ-aminopropyltriethoxysilane in 150 ml of xylene. The temperature rises to 130°–135° C. in the course of 16 hours and the methanol formed is distilled off. The reaction mixture is diluted with about 300 ml of xylene, the lithium amide is neutralised with acetic acid, and the solvent is evaporated, affording 36.8 g of a dark oil having the following structure:

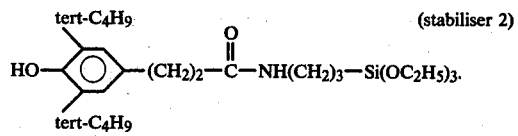

(stabiliser 2)

EXAMPLE 3

9.4 g (0.05 mole) of γ-aminopropyltriethoxysilane in 50 ml of toluene are added dropwise under nitrogen to 13.9 g (0.05 mole) of 4-hydroxy-3,5-di-tert-butylphenylpropionic acid in 100 ml of toluene. The reaction mixture is stirred for 16 hours at reflux temperature. The solvent is then evaporated, affording 20.3 g of a viscous oil having the structure:

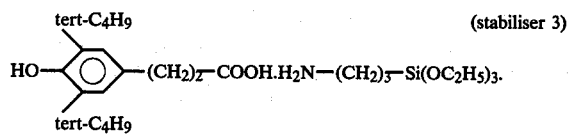

(stabiliser 3)

EXAMPLE 4

12.3 g (0.05 mole) of γ-glycidyloxypropyltrimethoxysilane are added dropwise under nitrogen at 25° C. to 11.05 g (0.05 mole) of 4-amino-2,6-di-tert-butylphenol in 250 ml of ethanol. The reaction mixture is kept for 16 hours at reflux temperature, then cooled, and the solvent is evaporated, affording a viscous oil (23 g) having the following structure:

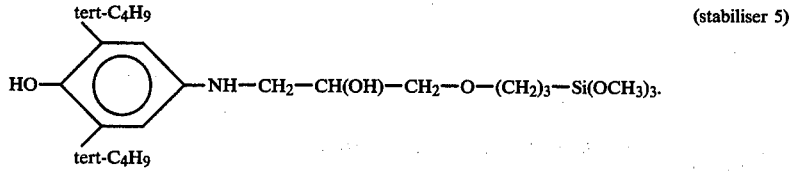

(stabiliser 5)

EXAMPLE 5

12.5 g (0.1 mole) of 2,4-dimethyl-6-aminophenol are dissolved in 150 ml of ethanol and then 23.6 g (0.1 mole) of γ-glycidyloxypropyltrimethoxysilane are slowly added dropwise to this solution. The reaction mixture is kept for 16 hours at reflux temperature. Working up as described in Example 4 yields 29.5 g of the following product:

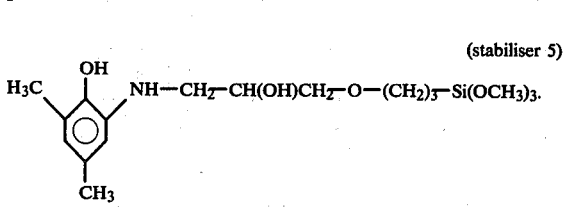

(stabiliser 5)

EXAMPLE 6:

A bomb tube is charged with 24.7 g (0.1 mole) of 4-allyl-2,6-di-tert-butylphenol, 12.1 g (0.1 mole) of trimethoxysilane and 0.5 g of hexachloroplatinic acid in 10 ml of isopropanol, and the mixture is heated under nitrogen to 180° C. The reaction mixture is cooled after 16 hours, the platinic acid filtered off, and the solvent evaporated. The residual viscous oil has the following structure:

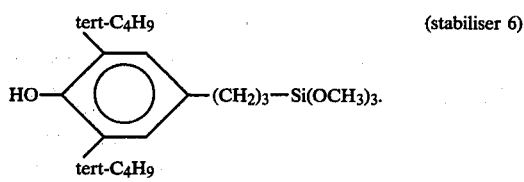

(stabiliser 6)

EXAMPLE 7

9.82 g (0.05 mole) of mercaptopropyltrimethoxysilane and 13.2 g (0.05 mole) of N-dimethyl-4-hydroxy-3,5-di-tert-butylbenzylamide are dissolved in 50 ml of dimethyl formamide and the mixture is heated under nitrogen to 100° C. The reaction mixture is cooled after 16 hours and the solvent is evaporated (in a high vacuum, drying for 4 hours at 80° C.). The residue consists of 18.9 g of a clear red oil having the following structure:

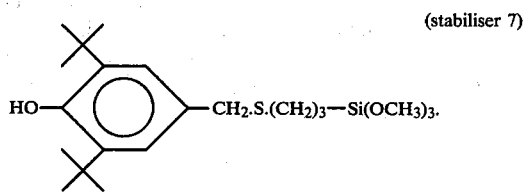

(stabiliser 7)

EXAMPLE 8

Oil oxidation test, standard version in accordance with ASTM D 2272 (rotary bomb oxidation test)

A sample of Shell rotary vacuum oil (viscosity 11 cS/100° C.), to which 0.25 g of stabiliser has been added, is oxidised in a glass vessel in an oxygen atmosphere together with 5 ml of distilled water and a brightly polished copper spiral which has been washed with petroleum and which acts as catalyst. The glass vessel is in a bomb of stainless steel fitted with a pressure gauge. The bomb rotates axially at 100 rpm and at an angle of 30° to the horizontal in an oil bath at 150° C. The initial oxygen pressure before heating is about 6 atmos. (90 psi), rises at 150° C. to just on 14 atmos. (200 psi) and remains constant until the onset of oxidation. The test is complete at a fall in pressure of about 1.7 atmos. (25 psi). The time in minutes is recorded.

| Stabiliser | Time in minutes until fall in pressure of about 25 psi Rot. Vac. P. Oil |
|---|---|
| without | 57 |
| 0.5% Nr. 1 | 185 |
| 0.25% Nr. 7 | 80 |

EXAMPLE 9

Oil Oxidation Test in Accordance with IP 280, "CIGRE" (modified, accelerated method IP 280)

Modified version with soluble Cu and Fe catalyst.

Conditions: introduction of oxygen over 4 hours at 150° C. (4 liters/$O_2$/h).

Determination of the acid number after completion of test: consumption of KOH in mg per g of test oil (reported in table).

Test oil: Shell rotary vacuum oil (viscosity 11 cS/100° C.).

TABLE

| Stabiliser | mg KOH/g |
|---|---|
| without | 2.5 |
| 0.5% Nr. 1 | 0.23 |
| 0.25% Nr. 7 | 0.93 |

EXAMPLE 10

TOST, oxidation characteristics of Vitrea 27 oil (ASTM D 943/DIN 51 587/IP 157)

The oil for testing is heated to 95° C. in the presence of water and an iron/copper catalyst, while measuring the time in hours in which the degree of neutralisation of the oil has reached a consumption of 2 mg of KOH/g (TOST life).

| Stabiliser | TOST life in hours |
|---|---|
| (0.25%) No. 1 | 1600 |
| none | 100 |

What is claimed is:

1. A compound of the formula I

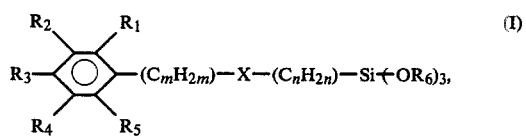

(I)

wherein one of $R_1$ and $R_3$ is hydrogen and the other is OH, each of $R_2$, $R_4$ and $R_5$ independently is $C_1$–$C_{12}$alkyl, $C_5$–$C_7$cycloalkyl, $C_6$–$C_{10}$aryl or $C_7$–$C_9$aralkyl, and $R_4$ and $R_5$ are also hydrogen, $R_6$ is $C_1$–$C_{18}$alkyl, each of m and n independently is an integer from 0 to 6, X is the direct bond, —O—, —S—, —N($R_7$)—, —Q—$R_8$— or

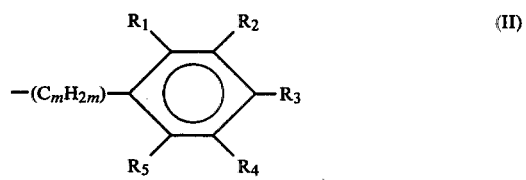

(II)

wherein $R_7$ represents hydrogen, $C_1$–$C_{12}$alkyl, phenyl or a group of the formula II

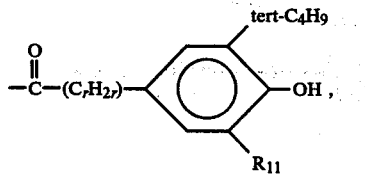                                        (IV)

wherein $R_1$, $R_2$, $R_3$, $R_4$, $R_5$ and m are as defined above, Q is —O— or —NH—, $R_8$ represents a group of the formula III

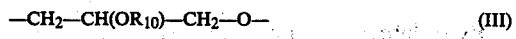 (III)

wherein $R_{10}$ is hydrogen, $C_1$-$C_{12}$alkyl or a group of the formula IV

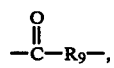, wherein r is an integer from 0 to 6, $R_{11}$ is hydrogen, $C_1$-$C_{12}$alkyl, $C_5$-$C_7$cycloalkyl, $C_6$-$C_{10}$aryl or $C_7$-$C_9$aralkyl, and $R_9$ is —O—, —NH—, —CH.$H_2$N—, —O—$CH_2CH_2$—S—,

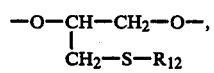

—O—$R_8$—, or a group of the formula V

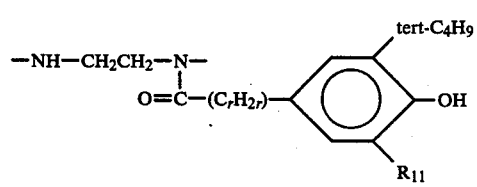 (V)

wherein $R_8$, $R_{11}$ and r are as defined above, and $R_{12}$ is $C_1$-$C_{18}$alkyl, $C_5$-$C_7$cycloalkyl, $C_6$-$C_{10}$aryl, $C_7$-$C_9$aralkyl or a group of the formulae VI or VII

 (VI)

or

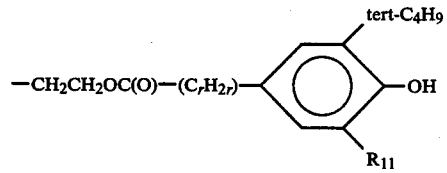 (VII)

wherein u is an integer from 1 to 6 and $R_{10}$, $R_{11}$ and r are as defined above.

2. A compound according to claim 1 of formula I, wherein $R_1$ and $R_5$ are hydrogen and $R_3$ is OH.

3. A compound according to claim 1 of formula I, wherein X is —N($R_7$)—.

4. A compound according to claim 1 of formula I, wherein m is 0 to 4 and n is 3.

5. A compound according to claim 1 of formula I, wherein $R_1$ is hydrogen, $R_3$ is OH and each of $R_2$, $R_4$ and $R_6$ independently is $C_1$-$C_{12}$alkyl and $R_4$ is also hydrogen, $R_5$ is hydrogen or $C_1$-$C_6$alkyl, m is an integer from 0 to 4 and n is 3, X is the direct bond, —O—, —S—, —N($R_7$)—, —O—$R_8$— or

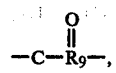, wherein $R_7$ is hydrogen or a group group of the formula II, in which $R_1$, $R_2$, $R_3$, $R_4$, $R_5$ and m are as defined above, Q is —O— or —NH—, $R_8$ is a group of the formula III, wherein $R_{10}$ is hydrogen, $C_1$-$C_{12}$alkyl or a group of the formula VI, wherein r is an integer from 0 to 4, $R_{11}$ is $C_1$-$C_{12}$alkyl, and $R_9$ is —O—, —NH—, —OH.$H_2$N—, —O—$CH_2$—$CH_2$—S—, —O$R_8$— or a group of the formula V, wherein $R_8$, r and $R_{11}$ have the above meanings.

6. A compound according to claim 1 of formula I, wherein $R_1$ and $R_5$ are hydrogen, $R_3$ is OH, $R_2$ is $C_1$-$C_8$alkyl, $R_4$ is $C_1$-$C_4$alkyl, $R_6$ is methyl or ethyl, m is an integer from 0 to 4 and n is 3, X is the direct bond, —O—, —S—, —N($R_7$)— or

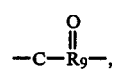, wherein $R_7$ is a group of the formula II, in which $R_1$, $R_2$, $R_3$, $R_4$, $R_5$ and m are as defined above, $R_9$ is —NH—, —O—$CH_2$—$CH_2$—S— or —O$R_8$—, wherein $R_8$ is a group of the formula III, in which $R_{10}$ is hydrogen or a group of the formula IV, wherein R is 2 and $R_{11}$ is $C_1$-$C_4$alkyl.

7. A compound according to claim 1 of formula I, wherein $R_1$ and $R_5$ are hydrogen, $R_3$ is OH, $R_2$ is methyl or tert-butyl, $R_4$ is tert-butyl, $R_6$ is methyl or ethyl, m is an integer from 1 to 3 and n is 3, X is the direct bond, —O—, —S—, —N($R_7$)— or

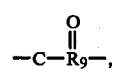, wherein $R_7$ is a group of the formula II, in which $R_1$, $R_2$, $R_3$, $R_4$, $R_5$ and m have the above meanings, $R_9$ is —NH— or —O$R_8$, wherein $R_8$ is a group of the formula III, in which $R_{10}$ is hydrogen.

8. A compound according to claim 1 of formula I, wherein X is —NH—$R_8$— or

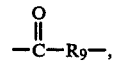, in which $R_8$ is as defined in claim 8 and $R_9$ is —OH.$H_2$N—.

9. A compound according to claim 1 of the formula

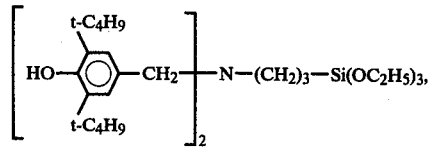

-continued
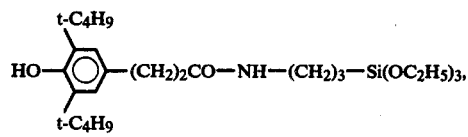
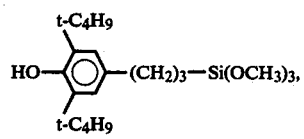
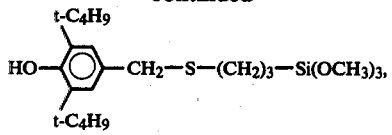
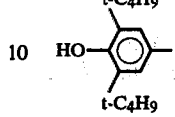
10. A lubricant additive containing a compound of the formula I according to claim 1.
11. The use of a compound of the formula I according to claim 1 as a lubricant additive.
* * * * *